United States Patent [19]

Amano et al.

[11] Patent Number: 4,774,150

[45] Date of Patent: Sep. 27, 1988

[54] THERMAL BARRIER COATING

[75] Inventors: Kagetaka Amano, Atsugi; Hiromitsu Takeda, Tokyo; Takao Suzuki, Ichikawa; Masaaki Tamatani, Fujisawa; Masayuki Itoh, Kawasaki; Yoshikazu Takahashi, Yokohama, all of Japan

[73] Assignee: Kabushiki Kaisha Toshiba, Kawasaki, Japan

[21] Appl. No.: 22,082

[22] Filed: Mar. 5, 1987

[30] Foreign Application Priority Data

Mar. 7, 1986 [JP] Japan ................................. 61-49905

[51] Int. Cl.$^4$ ......................... B32B 9/00; F01D 25/00
[52] U.S. Cl. .......................................... 428/690; 73/7;
116/200; 116/208; 415/118; 415/174; 416/241
B; 427/157; 427/419.3; 428/633; 428/699;
428/701; 428/702
[58] Field of Search ................ 428/688, 689, 690, 699,
428/701, 702, 633; 73/7; 116/200, 208;
415/118, 174; 416/241 B; 29/156.8 R, 407,
527.2; 427/157, 419.3

[56] References Cited

U.S. PATENT DOCUMENTS

| | | | |
|---|---|---|---|
| 2,976,716 | 3/1961 | De Haven | 73/7 |
| 4,269,903 | 5/1981 | Clingman et al. | 428/633 |
| 4,441,049 | 4/1984 | Verstegen et al. | 252/301.4 R |
| 4,473,513 | 9/1984 | Cusano et al. | 252/301.4 R |
| 4,532,938 | 8/1985 | Sippel | 73/7 |
| 4,563,297 | 1/1986 | Kokimoto et al. | 252/301.4 R |
| 4,600,659 | 7/1986 | Hong et al. | 428/472 |

Primary Examiner—George F. Lesmes
Assistant Examiner—James B. Monroe
Attorney, Agent, or Firm—Oblon, Fisher, Spivak, McClelland & Maier

[57] ABSTRACT

According to the present invention there is provided a thermal barrier coating wherein multilayers of (I) a $ZrO_2$ layer containing a luminous activator and stabilized by $Y_2O_3$, CaO, MgO or a mixture thereof and (II) a $ZrO_2$ layer containing a luminous activator different from that used in (I) and stabilized by $Y_2O_3$, CaO, MgO or a mixture thereof, or a $ZrO_2$ layer not containing a luminous activator and stablized by $Y_2O_3$ are stacked, and the layers at least under an uppermost layer opposite to a base member to be protected have a total thickness sufficient for exhibiting a thermal barrier effect. The present invention has as its object to provide a thermal barrier coating which allows non-destructive testing to determine whether it has a thickness sufficient for themal barrier effect.

8 Claims, No Drawings

THERMAL BARRIER COATING

BACKGROUND OF THE INVENTION

The present invention relates to a thermal barrier coating and, more particularly, to a thermal barrier coating which allows nondestructive testing to determine whether the coating has a thickness sufficient for thermal barrier effect.

A thin ceramic layer of about 0.3 to 0.5 mm in thickness is formed as a thermal barrier coating on the surface of a base member, such as a heat resistant alloy, of a hot component such as a turbine casing of a gas turbine.

A thermal barrier coating is usually formed by plasma spraying of zirconium oxide ($ZrO_2$) stabilized by yttrium oxide ($Y_2O_3$), calcium oxide (CaO), magnesium oxide (MgO) or a mixture thereof. When $ZrO_2$ undergoes temperature change from a high to room temperature, phase transformation occurs, and the crystal formation changes at various portions. A difference in crystal formation leads to a difference in the volume of respective portions, and hence degradation in the coating strength is inevitable. In order to prevent this, $Y_2O_3$, CaO, MgO or a mixture thereof is added as a solid solution to prevent phase transformation, thus increasing the strength. With this countermeasure, however, erosion of the coating due to collision of fine particles included in a high-temperature gas flow cannot be prevented.

A thermal barrier effect of a coating depends not only on its thermal conductivity but also on its thickness. More specifically, when a thermal barrier coating layer is thinner than a predetermined thickness, the thermal barrier effect is sharply decreased. It is conventionally known that a thermal barrier coating layer preferably has a thickness of more than 0.2 mm in order to provide a required thermal barrier effect.

When a thermal barrier coating is used in practice, however, it is eroded as described above, and its thickness is decreased and it cannot provide the predetermined thermal barrier effect.

Therefore, the remaining thickness of a thermal barrier coating must be detected during inspection. However, no effective nondestructive testing is available at the present. As a result, even when the current thermal barrier coating has a sufficient effect, a new thermal barrier coating is often formed, or even when the thermal barrier coating already lost its effect, it is often used without being replaced, causing great damage to the base member.

SUMMARY OF THE INVENTION

The present invention has been made in view of the above situation and has as its object to provide a thermal barrier coating which allows nondestructive testing to determine whether it has a thickness sufficient for thermal barrier effect.

The thermal barrier coating of the present invention is characterized in that it has a multilayered structure of (I) a $ZrO_2$ layer mixed with a luminous activator and stabilized by $Y_2O_3$, CaO, MgO or a mixture thereof, and (II) a $ZrO_2$ layer mixed with a luminous activator different from that used in (I) and stabilized by $Y_2O_3$, CaO, MgO or a mixture thereof, or a $ZrO_2$ layer not containing a luminous activator and stabilized by $Y_2O_3$, CaO, MgO or a mixture thereof, and layers at least under an uppermost layer opposite to a base member to be protected have a total thickness sufficient for exhibiting a thermal barrier effect.

The present invention utilizes the fact that, when $ZrO_2$ is irradiated with ultraviolet rays, its orbital electrons are excited to generate a pale blue fluorescence, and that, when various oxides are added to $ZrO_2$, the color of the fluorescence changes.

Regarding the above-mentioned $ZrO_2$ mixed with $Y_2O_3$ as the stabilizer, as the solid solution amount of $Y_2O_3$ is increased, the fluorescence changes from reddish to dark orange. Thus, in order to nondestructively and simply determine whether the thermal barrier coating has a thickness sufficient for thermal barrier effect, the thermal barrier coating may comprise two $ZrO_2$ layers having different $Y_2O_3$ contents and its lower layer formed on a base member to be protected may have a minimum necessary thickness sufficient for thermal barrier effect. This is because coloring of the upper layer and that of the lower layer which is exposed by wearing or damaging of the upper layer are different. However, since the difference in the coloring of the two layers of the thermal barrier coating is not apparent, it cannot be easily identified.

Therefore, according to the present invention, in order to cause an apparent difference in the coloring when the thermal barrier coating is irradiated with ultraviolet rays, the thermal barrier coating has a multilayered structure of (I) a $ZrO_2$ layer mixed with a luminous activator and stabilized by, for example, $Y_2O_3$ and (II) a $ZrO_2$ layer mixed with a luminous activator different from that used in (I) and stabilized by, for example, $Y_2O_3$, or a $ZrO_2$ layer not containing a luminous activator and stabilized by, for example, $Y_2O_3$. As examples of the luminous activator, $Bi_2O_3$, $TiO_2$, or $Tb_4O_7$, which emit blue-green fluorescence, or $Eu_2O_3$ or $Sm_2O_3$, which emit red fluorescence are available. Any other additive can be used if it can cause an apparent coloring difference from $ZrO_2$ mixed with only $Y_2O_3$. The content of the luminous activator is preferably less than 5% from the viewpoint of luminous efficacy and heat resistance.

Regarding the stacked layer structure, when its lowermost layer formed on the base member to be protected has at least the minimum thickness necessary to exhibit a thermal barrier effect, and when an upper layer is stacked on this lower-most layer to constitute a two-layer structure, the object of the present invention can be achieved. However, the lowermost layer can have a thickness greater than the minimum. The total thickness of the lowermost layer up to a certain layer other than the uppermost layer can have a sufficient thickness required for thermal barrier effect. In this case, if many layers are additionally stacked on the layers which provide a sufficient total thickness, they serve as a margin of the minimum thickness necessary for thermal barrier effect and are precautionary.

In this manner, if a thermal barrier coating is used with a knowledge about the fluorescent color of a "safety" layer having the minimum thickness necessary for thermal barrier effect, when this fluorescent color appears, use of the thermal barrier coating can be stopped, and a new thermal barrier coating can be replaced, thereby preventing damage to the base member.

When the stack layer structure is a two-layer structure, either of the layers (I) and (II) can be used as the lower layer. When the stacked layer structure is a more than three-layer structure, the stacked order of layers (I) and (II) can be reversed, as long as the fluorescent colors of adjacent layers are different.

DETAILED DESCRIPTION OF THE PREFERRED EMBODIMENTS

Example 1

A metal bonding layer of an Ni-Co-Cr-Al-Y alloy having a thickness of 100 μm was formed by plasma spraying on a test piece of a Ni-base superalloy IN738 (trademark of Inco. Ltd.), and $ZrO_2$ ceramic mixed with 1% of $TiO_2$ and 8% of $Y_2O_3$ was plasma sprayed in 8 passes onto the metal bonding layer at a rate of 25 μm/pass to form a lower layer having a thickness of 200 μm as part of a thermal barrier coating. $ZrO_2$ ceramic mixed with only 8% of $Y_2O_3$ was plasma sprayed in 4 passes on this lower layer in the same manner as in the formation of the lower layer, thereby forming an upper layer having a thickness of 100 μm. In this manner, a thermal barrier coating having a total thickness of 300 μm was formed. This coating was irradiated with ultraviolet rays having a wavelength of 254 nm. The coating exhibited a dark orange color.

The thermal barrier coating on the test piece was gradually removed by sand blasting using alumina. During this operation, the thickness of the thermal barrier coating was measured, ultraviolet rays having a wavelength of 254 nm were radiated, and the light emitted by the coating was observed. The fluorescent color changed from dark orange to green when the thickness of the thermal barrier coating layer was 200 μm.

From the above simulation testing, it was confirmed that whether a thermal barrier coating had a sufficient thickness could be nondestructively determined.

EXAMPLE 2

The lower layer of a thermal barrier coating was mixed with $Eu_2O_3$, in place of $TiO_2$, as a luminous activator. The same test as in Example 1 was performed. The fluorescent color changed from dark orange to light orange when the thickness of the thermal barrier coating was 200 μm.

$ZrO_2$ mixed with $TiO_2$ and stabilized by $Y_2O_3$, and $ZrO_2$ mixed with $Eu_2O_3$ and stabilized by $Y_2O_3$ were used as the lower and upper layers, respectively, of the thermal barrier coating. The same test as in Example 1 was performed. The fluorescent color noticably changed from light orange to green when the thickness of the heat shield coating was 200 μm.

In all of the above examples, the thermal barrier characteristic and the strength of the thermal barrier coating were not degraded by addition of a luminous activator.

EXAMPLE 3

A metal bonding layer of an Ni-Cr-Al-Y alloy having a thickness of 100 μm was formed by plasma spraying on the same type of test piece used in the above Examples. A 200-μm thick thermal barrier coating containing 1% of $EuO_2$, 8% of $Y_2O_3$, and the balance of $ZrO_2$, a 50-μm thick thermal barrier coating containing 0.5% of $TiO_2$, 8% of $Y_2O_3$, and the balance of $ZrO_2$, and a 50-μm thick thermal barrier coating containing 8% of $Y_2O_3$ and the balance of $ZrO_2$ were formed by plasma spraying on the metal bonding layer, thereby providing a thermal barrier coating having a total thickness of 300 μm. The same test as described above was performed. The thermal barrier coating was irradiated with ultraviolet rays. The fluorescence changed from dark orange to green, and then to light red. The green color, serving as a precaution signal for the light red color which indicated a minimum necessary thickness, was effectively observed. Also, the remaining thickness proportional to the time lapse could be roughly calculated.

What is claimed is:

1. A thermal barrier coating of multilayer structure supported by a base member, said multilayer structure, comprising:
   (I) a $ZrO_2$ layer containing a first luminous activator which is stabilized by $Y_2O_3$, CaO, MgO or a mixture thereof; and
   (II) a $ZrO_2$ layer containing a second luminous activator different from said first luminous activator and stabilized by $Y_2O_3$, CaO, MgO or a mixture thereof;
   each layer of said multilayer structure containing a luminous activator which generates a fluorescent color different from those generated from adjacent layers, when said layers are subjected to ultraviolet radiation, wherein the degree of wear of said thermal barrier coating is detectable by observing the fluorescent color generate by said structure when the same is irradiated with ultraviolet radiation, and wherein the lowermost layer of said layers I and II is of a minimum thickness to ensure a thermal barrier effect.

2. The thermal barrier coating according to claim 1, wherein the content of the luminous activator in each layer is less than 5% by weight.

3. The thermal barrier coating according to claim 1, wherein said thermal barrier coating comprises in sequence one layer of (I), coated onto said base member, and one layer of (II), coated onto said layer of (I).

4. The thermal barrier coating according to claim 3, wherein said luminous activator present in layer (I) is $Bi_2O_3$, $TiO_2$ or $Tb_4O_7$ which generates a blue-green fluorescence, and said luminous activator in layer (II) is $Eu_2O_3$ or $Sm_2O_3$ which generates light of red fluorescence.

5. The thermal barrier coating according to claim 3, wherein said luminous activator in layer (I) is $Eu_2O_3$ or $Sm_2O_3$, which generates light of red fluorescence, and said luminous activator in layer (II) is $Bi_2O_3$, $TiO_2$ or $Tb_4O_7$, which generates light of a blue-green fluorescence.

6. A thermal barrier coating of multilayer structure supported by a base member, said multilayer structure comprising:
   (I) a $ZrO_2$ layer containing a luminous activator which is stabilized by $Y_2O_3$, CaO, MgO or a mixture thereof; and
   (II) a $ZrO_2$ layer which does not contain a luminous activator and which is stabilized by $Y_2O_3$;
   said layer (I) of said multilayer structure containing said luminous activator generating a fluorescent color when said layers are subjected to ultraviolet radiation thereby providing an indication of the degree of wear of said thermal barrier coating by observing the fluorescent color or lack thereof generated by said structure when the same is irradiated with said ultraviolet radiation depending upon whether the ultraviolet light impinges on said layer (I) or said layer (II), and wherein the lowermost layer of said layers I and II is of minimum thickness to ensure a thermal barrier effect.

7. The thermal barrier coating according to claim 6, wherein said thermal barrier coating comprises one layer of (I) and one layer of (II).

8. The thermal barrier coating according to claim 6, wherein the content of the luminous activator in said layer (I) is less than 5% by weight.

* * * * *